US007309947B2

(12) United States Patent
Takeuchi et al.

(10) Patent No.: US 7,309,947 B2
(45) Date of Patent: Dec. 18, 2007

(54) PIEZOELECTRIC TRANSDUCER INCLUDING A PLURALITY OF PIEZOELECTRIC MEMBERS

(75) Inventors: Takashi Takeuchi, Tochigi-ken (JP); Tomohisa Imamura, Tochigi-ken (JP); Takashi Owaga, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 45 days.

(21) Appl. No.: 10/883,733

(22) Filed: Jul. 6, 2004

(65) Prior Publication Data

US 2005/0023934 A1 Feb. 3, 2005

(30) Foreign Application Priority Data

Jul. 8, 2003 (JP) ............................ 2003-193858

(51) Int. Cl.
*H04R 17/00* (2006.01)
*H01L 41/08* (2006.01)
*A61B 8/14* (2006.01)

(52) U.S. Cl. ...................... 310/334; 600/459; 600/437; 367/155; 367/157

(58) Field of Classification Search ................ 310/334; 600/437, 459; 367/155, 157
See application file for complete search history.

(56) References Cited

U.S. PATENT DOCUMENTS

| | | | | |
|---|---|---|---|---|
| 4,217,684 | A * | 8/1980 | Brisken et al. | 29/25.35 |
| 4,287,770 | A * | 9/1981 | Weyns | 310/334 |
| 4,460,841 | A * | 7/1984 | Smith et al. | 310/334 |
| 5,250,869 | A * | 10/1993 | Ishikawa et al. | 310/334 |
| 5,350,964 | A * | 9/1994 | Hara et al. | 310/357 |
| 5,438,554 | A * | 8/1995 | Seyed-Bolorforosh et al. | 310/334 |
| 5,657,295 | A * | 8/1997 | Howard | 367/140 |
| 6,201,900 | B1 * | 3/2001 | Hossack et al. | 600/437 |
| 6,465,937 | B1 * | 10/2002 | Chen et al. | 310/360 |
| 2004/0032188 | A1 * | 2/2004 | Bhardwaj | 310/334 |

FOREIGN PATENT DOCUMENTS

| | | |
|---|---|---|
| EP | 0480045 A1 * | 4/1992 |
| JP | 03-270599 | 12/1991 |

* cited by examiner

*Primary Examiner*—J. San Martin
(74) *Attorney, Agent, or Firm*—Oblon, Spivak, McClelland, Maier & Neustadt, P.C.

(57) ABSTRACT

A piezoelectric transducer for an ultrasonic scan is provided. The transducer includes a plurality of piezoelectric members arrayed. The plurality of piezoelectric members have different compositions parts in a slice direction so that an ultrasonic beam is focused in the slice direction.

14 Claims, 9 Drawing Sheets

PIEZOELECTRIC TRANSDUCER INCLUDING A PLURALITY OF PIEZOELECTRIC MEMBERS

CROSS-REFERENCE TO RELATED APPLICATION

This application is based upon and claims the benefit of priority from prior Japanese Patent Application No. P2003-193858, filed on Jul. 8, 2003, the entire content of which is incorporated herein by reference.

BACKGROUND OF THE INVENTION

1. Field of the Invention

The present invention relates to a piezoelectric transducer, an ultrasonic transducer which includes the piezoelectric transducer and is used in an ultrasonic scan, an ultrasonic probe including the ultrasonic transducer, and an ultrasound imaging apparatus including such an ultrasonic probe. The present invention further relates to a method of making a plurality of the piezoelectric transducers.

2. Discussion of the Background

An ultrasound imaging apparatus is well known to be used for medical purposes as an ultrasound diagnosis apparatus. The ultrasound diagnosis apparatus scans a patient's body by transmitting ultrasound pulses from an ultrasonic transducer and prepares ultrasound images of the inside of the patient's body based on echo signals caused by acoustic impedance mismatching inside the patient's body.

An ultrasonic transducer typically includes a plurality of transducer elements which are arrayed along a scan direction of the above scan. The transducer elements vibrate and generate the ultrasound pulses which are transmitted to the patient's body. The transducer elements also receive the echo signals from the body. The transducer elements have a flat strength along a direction perpendicular to the scan direction. Such a direction perpendicular to the scan direction is hereinafter referred to as a slice direction whether the scan is conducted at a fixed position or at various positions along the slice direction. The transducer elements also form a focal point at a certain depth inside the patient's body by that a delay difference is given to the generated ultrasound pulses by an acoustic lens provided in the ultrasonic transducer.

However, there is a limit to improve a behavior of an ultrasonic pulse beam convergence provided by the acoustic lens. Therefore, ultrasound acoustic pressure is weighted along the slice direction so as to improve the convergence behavior.

For example, Japanese Patent Application Publication No. PH11-146492 discloses an ultrasonic transducer in which an acoustic matching material attached to a piezoelectric transducer is provided with a plurality of gutters along a scan direction so as to give weightings along the slice direction.

Also for example, Japanese Patent Application Publication No. PH05-23331 discloses an ultrasonic transducer in which a piezoelectric transducer and one of electrode plates are divided into plural portions in the slice direction. Voltages to be applied to the electrode plate are weighted differently among the divided plural portions of the electrode plate.

In the above first example, there is a problem that the piezoelectric transducer cannot transmit ultrasound pulses and receive echo signals in some parts, which results in high side lobes. In addition, an ultrasonic transducer and an ultrasonic probe become complicated in their structures.

Such structures lead to an increase in manufacturing processes and accordingly to increased manufacturing cost.

In the above second example, there is a problem that an electric circuitry scale becomes large because it is necessary to apply different voltages to divided electrode portions. As a result, manufacturing cost of the ultrasonic transducer increases. In addition, manufacturing processes of the ultrasonic transducer increase for the above reason.

SUMMARY OF THE INVENTION

According to the first aspect of the present invention, there is provided a piezoelectric transducer for an ultrasonic scan. The transducer includes a plurality of piezoelectric members arrayed. The plurality of piezoelectric members have different compositions parts in a slice direction so that an ultrasonic beam is focused in the slice direction.

According to the second aspect of the present invention, there is provided a piezoelectric transducer for an ultrasonic scan. The transducer includes a plurality of piezoelectric members arrayed in contact along a direction perpendicular to a scan plane by the ultrasonic scan. The plurality of piezoelectric members are made of predetermined compositions so as to have predetermined electromechanical coupling factors. The plurality of piezoelectric members are arrayed in an order that the predetermined electromechanical coupling factors gradually decrease towards one and the other ends of the array from a middle of the array.

According to the third aspect of the present invention, there is provided a piezoelectric transducer for an ultrasonic scan. The transducer includes a plurality of piezoelectric members arrayed in contact along a direction perpendicular to a scan plane by the ultrasonic scan. The plurality of piezoelectric members are made of predetermined compositions so as to have predetermined relative dielectric constants. The plurality of piezoelectric members are arrayed in an order that the predetermined relative dielectric constants gradually increase towards one and the other ends of the array from a middle of the array.

According to the fourth aspect of the present invention, there is provided a piezoelectric transducer for an ultrasonic scan. The transducer includes a plurality of piezoelectric members arrayed in contact along a direction perpendicular to a scan plane by the ultrasonic scan. The first piezoelectric member positioned in a middle of the plurality of piezoelectric members is made of a first composition so as to have a first electromechanical coupling factor. The second piezoelectric member positioned at one end of the plurality of piezoelectric members is made of a second composition so as to have a second electromechanical coupling factor. The second electromechanical coupling factor is lower than the first electromechanical coupling factor. The third piezoelectric member positioned at another end of the plurality of piezoelectric members is made of a third composition so as to have a third electromechanical coupling factor. The third electromechanical coupling factor is lower than the first electromechanical coupling factor. The fourth piezoelectric member of the plurality of piezoelectric members, positioned between the first and second piezoelectric members, is made of a fourth composition so as to have a fourth electromechanical coupling factor. The fourth electromechanical coupling factor is lower than the first electromechanical coupling factor and higher than the second electromechanical coupling factor. The fifth piezoelectric member of the plurality of piezoelectric members, positioned between the first and third piezoelectric members, is made of a fifth composition so as to have a fifth electromechanical coupling factor. The fifth electromechanical coupling factor is lower than the first electromechanical coupling factor and higher than the third electromechanical coupling factor. The sixth piezoelectric member of the plurality of piezoelectric members, positioned between the first and fourth piezoelectric members, is made of a sixth composition so as to have a sixth electromechanical coupling factor. The sixth electromechanical coupling factor is lower than the first electromechanical coupling factor and substantially identical to or higher than the fourth electromechanical coupling factor. The seventh piezoelectric member of the plurality of piezoelectric members, positioned between the first and fifth piezoelectric members, is made of a seventh composition so as to have a seventh electromechanical coupling factor. The seventh electromechanical coupling factor is lower than the first electromechanical coupling factor and substantially identical to or higher than the fifth electromechanical coupling factor.

According to the fifth aspect of the present invention, there is provided a piezoelectric transducer for an ultrasonic scan. The transducer includes a plurality of piezoelectric members arrayed in contact along a direction perpendicular to a scan plane by the ultrasonic scan. The first piezoelectric member positioned in a middle of the plurality of piezoelectric members is made of a first composition so as to have a first relative dielectric constant. The second piezoelectric member positioned at one end of the plurality of piezoelectric members is made of a second composition so as to have a second relative dielectric constant. The second relative dielectric constant is higher than the first relative dielectric constant. The third piezoelectric member positioned at another end of the plurality of piezoelectric members is made of a third composition so as to have a third relative dielectric constant. The third relative dielectric constant is higher than the first relative dielectric constant. The fourth piezoelectric member of the plurality of piezoelectric members, positioned between the first and second piezoelectric members, is made of a fourth composition so as to have a fourth relative dielectric constant. The fourth relative dielectric constant is higher than the first relative dielectric constant and is lower than the second relative dielectric constant. The fifth piezoelectric member of the plurality of piezoelectric members, positioned between the first and third piezoelectric members, is made of a fifth composition so as to have a fifth relative dielectric constant. The fifth relative dielectric constant is higher than the first relative dielectric constant and is lower than the third relative dielectric constant. The sixth piezoelectric member of the plurality of piezoelectric members, positioned between the first and fourth piezoelectric members, is made of a sixth composition so as to have a sixth relative dielectric constant. The sixth relative dielectric constant is higher than the first relative dielectric constant and is substantially identical to or lower than the fourth relative dielectric constant. The seventh piezoelectric member of the plurality of piezoelectric members, positioned between the first and fifth piezoelectric members, is made of a seventh composition so as to have a seventh relative dielectric constant. The seventh relative dielectric constant is higher than the first relative dielectric constant and is substantially identical to or lower than the fifth relative dielectric constant.

According to the sixth aspect of the present invention, there is provided an ultrasonic transducer for an ultrasonic scan. The transducer includes a piezoelectric transducer, a pair of electrodes, and an acoustic lens. The piezoelectric transducer is configured to generate an ultrasound. The piezoelectric transducer includes a plurality of piezoelectric members arrayed in contact along a direction perpendicular to a scan plane by the ultrasonic scan. The pair of electrodes are configured to activate the piezoelectric transducer when a predetermined voltage is applied to the electrodes. The electrodes are provided on one and the opposite sides of the piezoelectric transducer, perpendicular to the array and the scan plane. The acoustic lens is provided on one side of one of the electrodes opposite to a side where the one electrode faces the piezoelectric transducer. The generated ultrasound is transmitted through the acoustic lens. The plurality of piezoelectric members are made of predetermined compositions so as to have predetermined electromechanical coupling factors. The plurality of piezoelectric members are arrayed in an order that the predetermined electromechanical coupling factors gradually decrease towards one and the other ends of the array from a middle of the array.

According to the seventh aspect of the present invention, there is provided an ultrasonic transducer for an ultrasonic scan. The transducer includes a piezoelectric transducer, a pair of electrodes, and an acoustic lens. The piezoelectric transducer is configured to generate an ultrasound. The piezoelectric transducer includes a plurality of piezoelectric members arrayed in contact along a direction perpendicular to a scan plane by the ultrasonic scan. The pair of electrodes are configured to activate the piezoelectric transducer when a predetermined voltage is applied to the electrodes. The electrodes are provided on one and the opposite sides of the piezoelectric transducer, perpendicular to the array and the scan plane. The acoustic lens is provided on one side of one of the electrodes opposite to a side where the one electrode faces the piezoelectric transducer. The generated ultrasound is transmitted through the acoustic lens. The plurality of piezoelectric members are made of predetermined compositions so as to have predetermined relative dielectric constants. The plurality of piezoelectric members are arrayed in an order that the predetermined relative dielectric constants gradually increase towards one and the other ends of the array from a middle of the array.

According to the eighth aspect of the present invention, there is provided an ultrasonic probe which is connectable to a main unit of an ultrasound imaging apparatus. The probe includes an ultrasonic transducer The ultrasonic transducer is configured to perform an ultrasonic scan. The ultrasonic transducer includes a piezoelectric transducer, a first electrode facing to one side of the piezoelectric transducer, and a second electrode facing to the opposite side of the piezoelectric transducer. The piezoelectric transducer includes a plurality of piezoelectric members arrayed in contact along a direction perpendicular to a scan plane by the ultrasonic scan. The plurality of piezoelectric members are made of predetermined compositions so as to have predetermined electromechanical coupling factors. The plurality of piezoelectric members are arrayed in an order that the predetermined electromechanical coupling factors gradually decrease towards one and the other ends of the array from a middle of the array.

According to the ninth aspect of the present invention, there is provided an ultrasonic probe which is connectable to a main unit of an ultrasound imaging apparatus. The probe includes an ultrasonic transducer The ultrasonic transducer is configured to perform an ultrasonic scan. The ultrasonic transducer includes a piezoelectric transducer, a first electrode facing to one side of the piezoelectric transducer, and a second electrode facing to the opposite side of the piezoelectric transducer. The piezoelectric transducer includes a plurality of piezoelectric members arrayed in contact along a direction perpendicular to a scan plane by the ultrasonic scan. The plurality of piezoelectric members are made of predetermined compositions so as to have predetermined relative dielectric constants. The plurality of piezoelectric members are arrayed in an order that the predetermined relative dielectric constants gradually increase towards one and the other ends of the array from a middle of the array.

According to the tenth aspect of the present invention, there is provided an ultrasound imaging apparatus. The apparatus includes an ultrasonic probe and a main unit. The ultrasonic probe includes a piezoelectric transducer and is configured to perform an ultrasonic scan. The main unit is coupled to the ultrasonic probe and has a processor. The processor is configured to process a data obtained from the ultrasonic scan. The piezoelectric transducer includes a plurality of piezoelectric members arrayed in contact along a direction perpendicular to a scan plane by the ultrasonic scan. The plurality of piezoelectric members are made of predetermined compositions so as to have predetermined electromechanical coupling factors. The plurality of piezoelectric members are arrayed in an order that the predetermined electromechanical coupling factors gradually decrease towards one and the other ends of the array from a middle of the array.

According to the eleventh aspect of the present invention, there is provided an ultrasound imaging apparatus. The apparatus includes an ultrasonic probe and a main unit. The ultrasonic probe includes a piezoelectric transducer and is configured to perform an ultrasonic scan. The main unit is coupled to the ultrasonic probe and has a processor. The processor is configured to process a data obtained from the ultrasonic scan. The piezoelectric transducer includes a plurality of piezoelectric members arrayed in contact along a direction perpendicular to a scan plane by the ultrasonic scan. The plurality of piezoelectric members are made of predetermined compositions so as to have predetermined relative dielectric constants. The plurality of piezoelectric members are arrayed in an order that the predetermined relative dielectric constants gradually increase towards one and the other ends of the array from a middle of the array.

According to the twelfth aspect of the present invention, there is provided a method for making a plurality of piezoelectric transducers. The method begins by preparing a plurality of piezoelectric sheets. The plurality of piezoelectric sheets are made of predetermined compositions so as to have predetermined electromechanical coupling factors. The method continues by layering the plurality of piezoelectric sheets in an order that the predetermined electromechanical coupling factors gradually decrease towards one and the other ends of the layer from a middle of the layer. The method further continues by sintering the layered piezoelectric sheets so as to obtain a layered piezoelectric block, and cutting the layered piezoelectric block, along a direction perpendicular to the layer, into the plurality of piezoelectric transducers. Each of the piezoelectric transducers has an array of a plurality of piezoelectric members.

According to the thirteenth aspect of the present invention, there is provided a method for making a plurality of piezoelectric transducers. The method begins by preparing a plurality of piezoelectric sheets. The plurality of piezoelectric sheets are made of predetermined compositions so as to have predetermined relative dielectric constants. The method continues by layering the plurality of piezoelectric sheets in an order that the predetermined relative dielectric constants gradually increase towards one and the other ends of the layer from a middle of the layer. The method further continues by sintering the layered piezoelectric sheets so as to obtain a layered piezoelectric block, and cutting the layered piezoelectric block, along a direction perpendicular to the layer, into the plurality of piezoelectric transducers. Each of the piezoelectric transducers has an array of a plurality of piezoelectric members.

According to the fourteenth aspect of the present invention, there is provided a piezoelectric transducer for an ultrasonic scan. The transducer includes a plurality of piezoelectric members arrayed in contact along a direction perpendicular to a scan plane by the ultrasonic scan. The plurality of piezoelectric members are made of predetermined compositions so as to have predetermined characteristics. The plurality of piezoelectric members are arrayed based on the predetermined characteristics in accordance with a predetermined set of weighting values.

BRIEF DESCRIPTION OF THE DRAWINGS

A more complete appreciation of embodiments of the present invention and many of its attendant advantages will be readily obtained by reference to the following detailed description considered in connection with the accompanying drawings, in which.

DESCRIPTION OF THE PREFERRED EMBODIMENTS

Figure 6A:
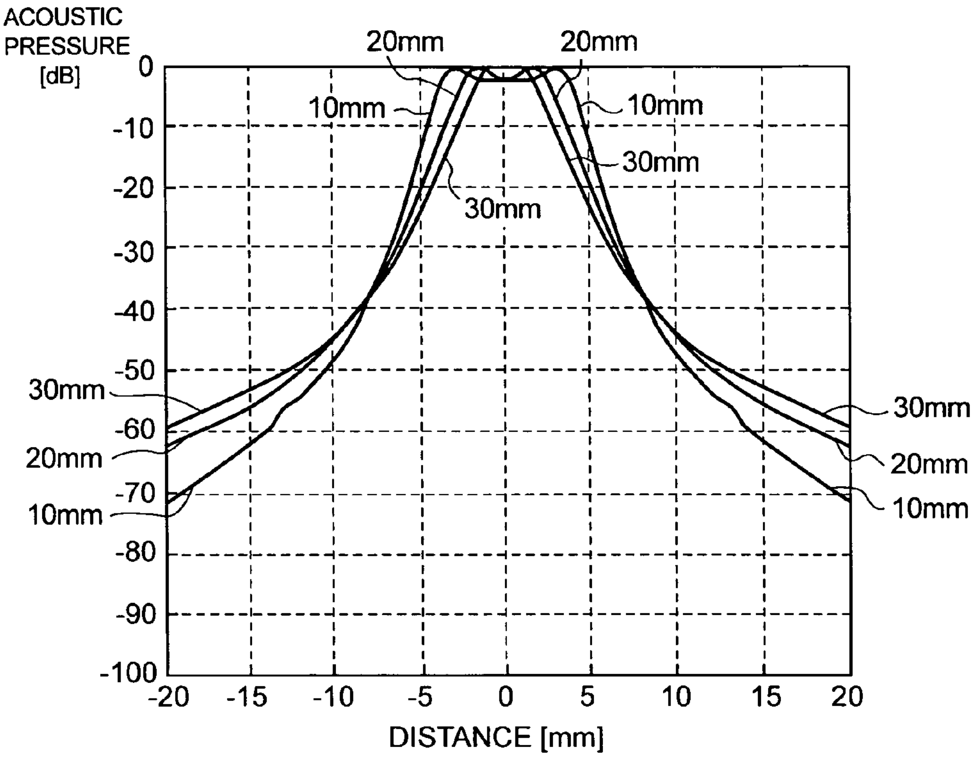
FIG. 6A (PRIOR ART)
FIGS. 6A and 6B are charts showing distributions of acoustic pressure in the reception of a prior art ultrasonic transducer in which no weighting is applied.
Figure 6B:
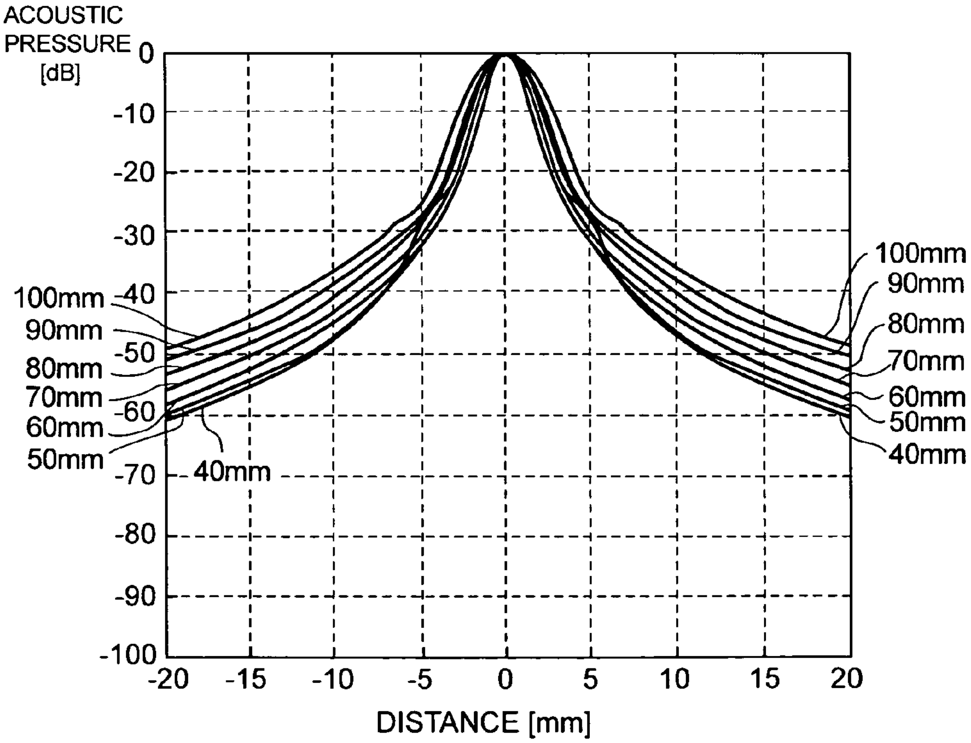
FIG. 6B (PRIOR ART)
Figure 7:
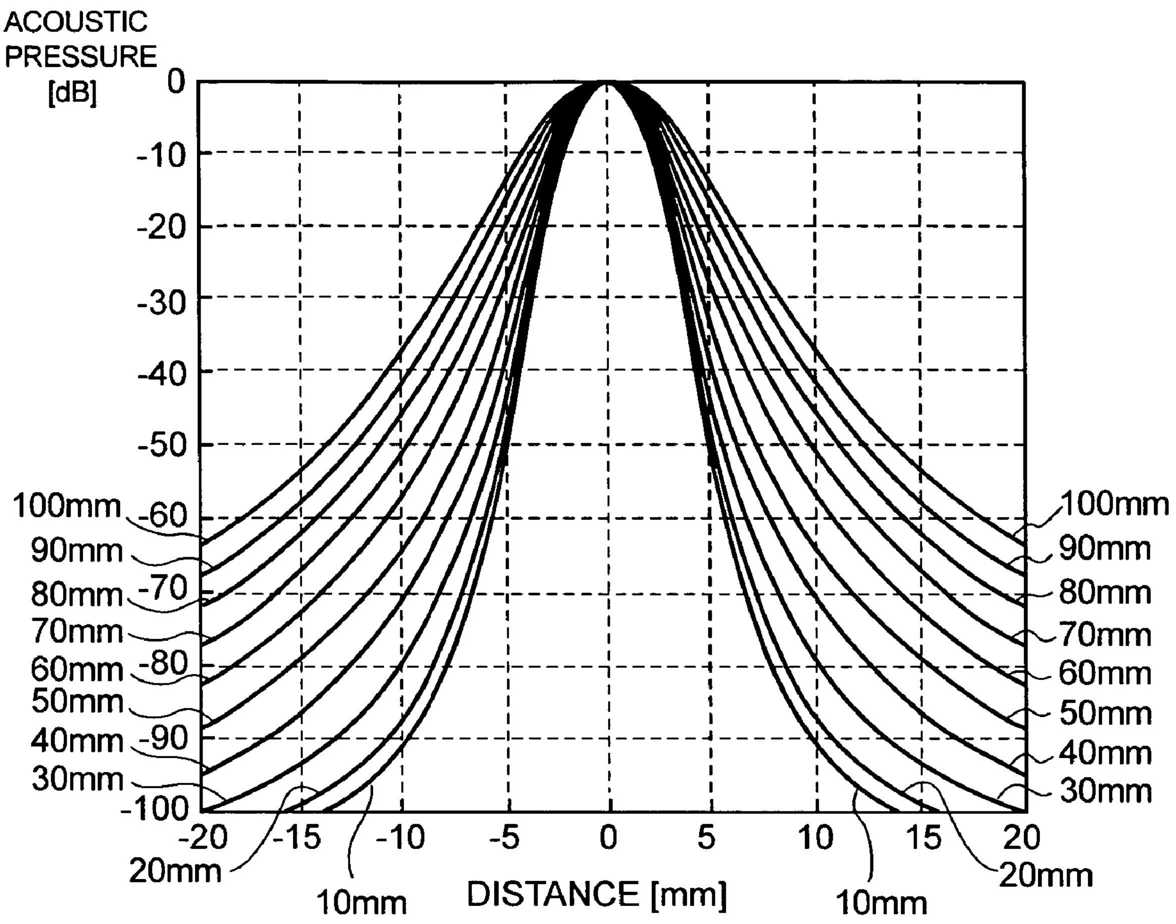
FIG. 7 is a chart showing distributions of acoustic pressure in the reception of the ultrasonic transducer according to the first embodiment.
Figure 8:
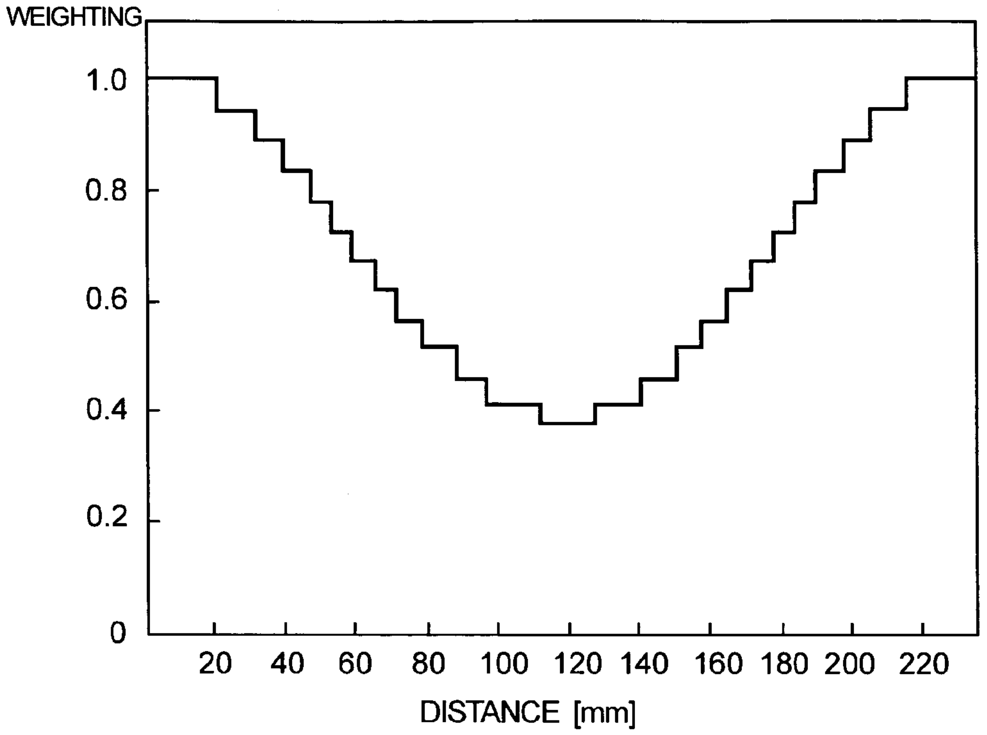
FIG. 8 is a chart showing an example of weighting according to the second embodiment.
Figure 9:
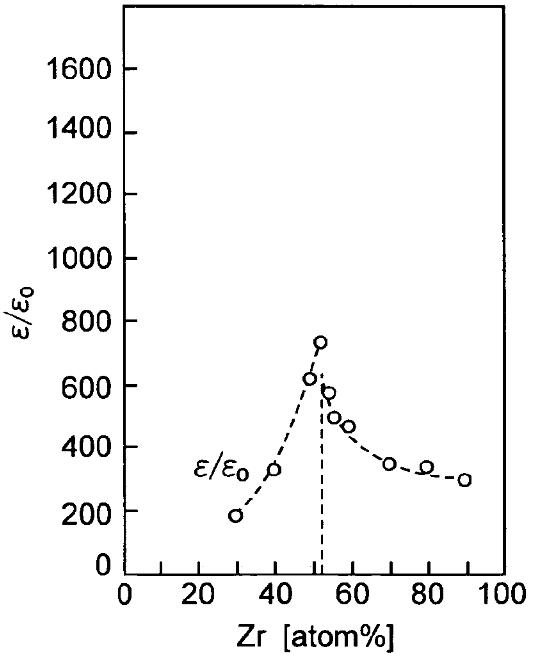
FIG. 9 is a chart showing a typical relationship between concentrations of zircon and relative dielectric constants.

Embodiments of the ultrasound diagnosis apparatus will be described with reference to the accompanying drawings. FIGS. 1 to 7 pertain to the first embodiment. FIGS. 8 to 10 pertain to the second embodiment.

First Embodiment

Figure 1:
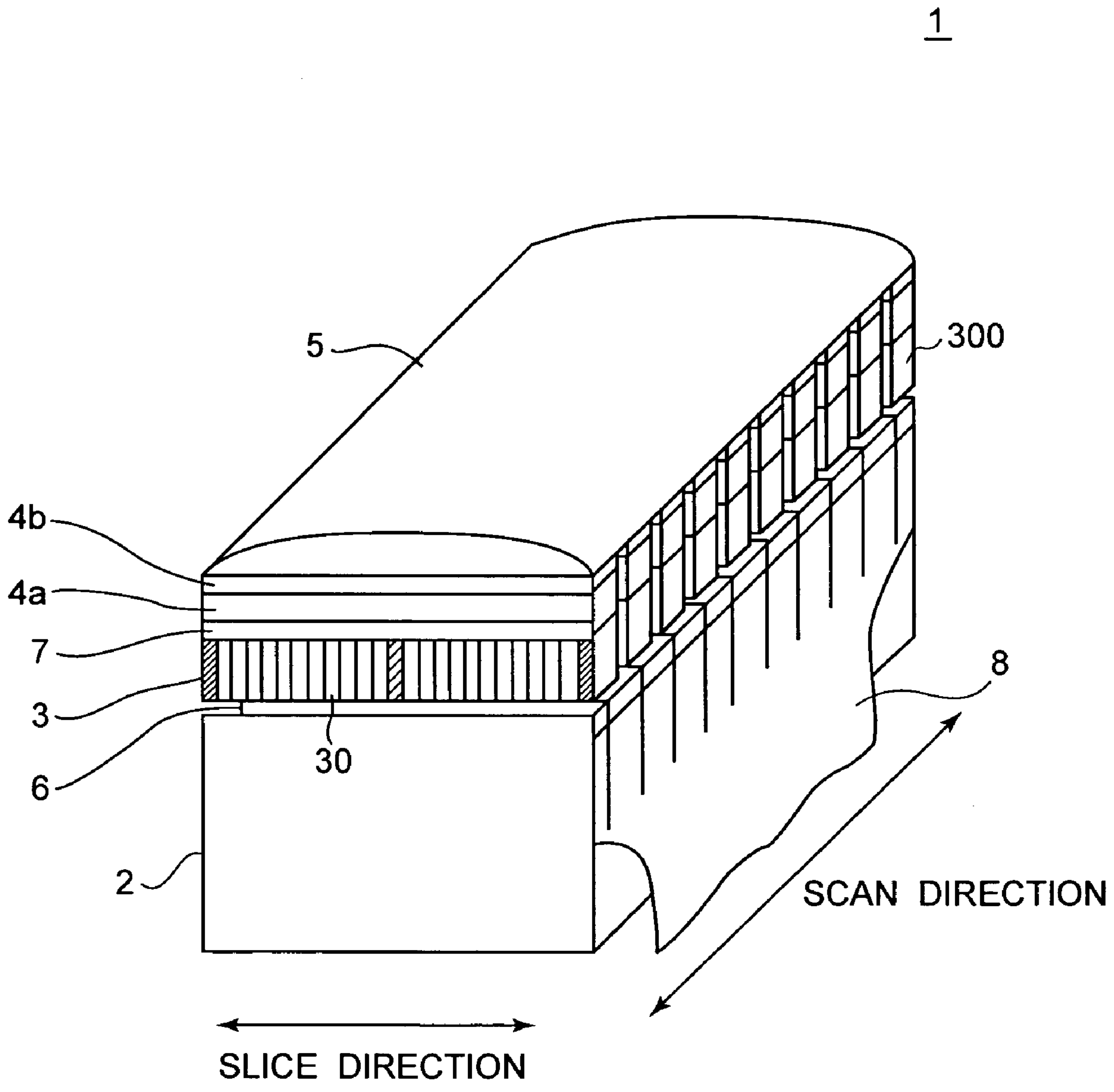
FIG. 1 is an illustration showing an exemplary configuration of an ultrasonic transducer according to the first embodiment.

FIG. 1 is an illustration showing an exemplary configuration of an ultrasonic transducer according to the first embodiment. The ultrasonic transducer can be used for an ultrasonic scan and be provided at a head of an ultrasonic probe which can be a part of an ultrasound imaging apparatus, such as, for example, an ultrasound flaw detector (or a reflectoscope) for detecting flaws caused inside a welded part of metals or an ultrasound diagnosis apparatus for the purpose of medical diagnoses The first embodiment will be described when the ultrasonic transducer is used for such an ultrasound diagnosis apparatus.

As shown in FIG. 1, an ultrasonic transducer 1 includes a back surface material 2, a piezoelectric transducer 3, a first acoustic matching layer 4*a*, a second acoustic matching layer 4*b*, an acoustic lens 5, electrodes 6 and 7, and a flexible printed wiring board 8. The piezoelectric transducer 3 is formed of (or includes) a plurality of transducer elements 300. The transducer elements 300 are arranged in an array form along a scan direction of ultrasound generated from the transducer elements 300. Along a slice direction of the piezoelectric transducer 3, the piezoelectric transducer 3 is made of a plurality of layers. Each layer is a predetermined piezoelectric member 30. The piezoelectric transducer 3 will be described in detail later.

When the piezoelectric transducer 3 transmits ultrasound to the patient's body or receives the echo signals from the patient's body, the piezoelectric transducer 3 oscillates and produces ultrasound vibration. The back surface material 2 attenuates and absorbs components of the ultrasound vibration which are not needed for image extraction in the ultrasound diagnosis apparatus.

The electrode 6 is provided on one side of the piezoelectric transducer 3. For example, as shown in FIG. 1, the electrode 6 is provided close to the back surface material 2 and forms a plurality of individual electrode elements. Each individual electrode element is provided in correspondence with one transducer element 300. Similarly, the electrode 7 is provided on the opposite side of the piezoelectric transducer 3. For example, the electrode 7 is provided close to the second acoustic matching layer 4*b* and forms a plurality of individual electrode elements. Each individual electrode element is provided in correspondence with one transducer element 300. One electrode element of the electrode 6 and one electrode element of the electrode 7 corresponding to the same transducer element 300 can be in pairs. Alternatively, two or more of the adjacent transducer elements 300 may be provided with one electrode element of the electrode 6 and one electrode element of the electrode 7. Such one electrode element of the electrode 6 and one electrode element of the electrode 7 can be in pairs. In this alternative case, the two or more adjacent transducer elements 300, commonly provided with a pair of one electrode element of the electrode 6 and one electrode element of the electrode 7, operate as if they constitute one transducer element.

The electrode 6 may be connected to the flexible printed wiring board 8. The electrode 7 may also be connected to the flexible printed wiring board 8. The electrode 6 is connected to signal lines (not shown in FIG. 1) through the flexible printed wiring board 8. The signal lines correspond to electrode elements. The electrode 7 is grounded through the flexible printed wiring board 8. Alternatively, the electrode 7 may be connected to an earth board while the electrode 6 is connected to the flexible printed wiring board 8. The earth board may be connected to the flexible printed wiring board 8.

High voltages are applied between the electrodes 6 and 7 through the flexible printed wiring board 8. To be precise, such voltages are applied to predetermined electrode elements in the element-by-element manner, along the scan direction. The piezoelectric transducer 3 vibrates in response to the voltage supply between the electrodes 6 and 7.

The first and second acoustic matching layers 4*a* and 4*b* are provided on an ultrasound reception surface side of the ultrasonic transducer 1. Although the first and second acoustic matching layers 4*a* and 4*b* are provided as a bilayer configuration in FIG. 1, a single layer or more than two layers may be used as an acoustic matching layer configuration. The first and second acoustic matching layers 4*a* and 4*b* are provided over the piezoelectric transducer 3 (or the electrode 7). The first and second acoustic matching layers 4*a* and 4*b* are covered by the acoustic lens 5. The first and second acoustic matching layers 4*a*, 4*b* and also the acoustic lens 5 limit a signal loss generated due to an acoustic impedance difference from a body surface of the patient.

The acoustic lens 5 is attached to the body surface of the patient when the ultrasound pulses are transmitted and resulting echo signals are received. The transmitted ultrasound pulses are acoustically focused at a predetermined depth of the patient's body in the slice direction. In the scan direction, the transmitted ultrasound pulses are acoustically focused by controlling to change transmission/reception timings of the arrayed transducer elements 300.

Based on the above configuration, when a predetermined voltage is applied to the electrodes 6 and 7, the piezoelectric transducer 3 generates ultrasound pulses by a piezoelectric effect. The generated ultrasound pulses are transmitted to an object to be diagnosed such as a tumor or a diseased part. The transmitted ultrasound pulses return as echo signals from interfaces of tissues which have different acoustic impedances, respectively. The echo signals are received and converted into electric signals by the piezoelectric transducer 3. Based on the electric signals, internal conditions of the object are extracted as one or more ultrasound images.

Figure 2:
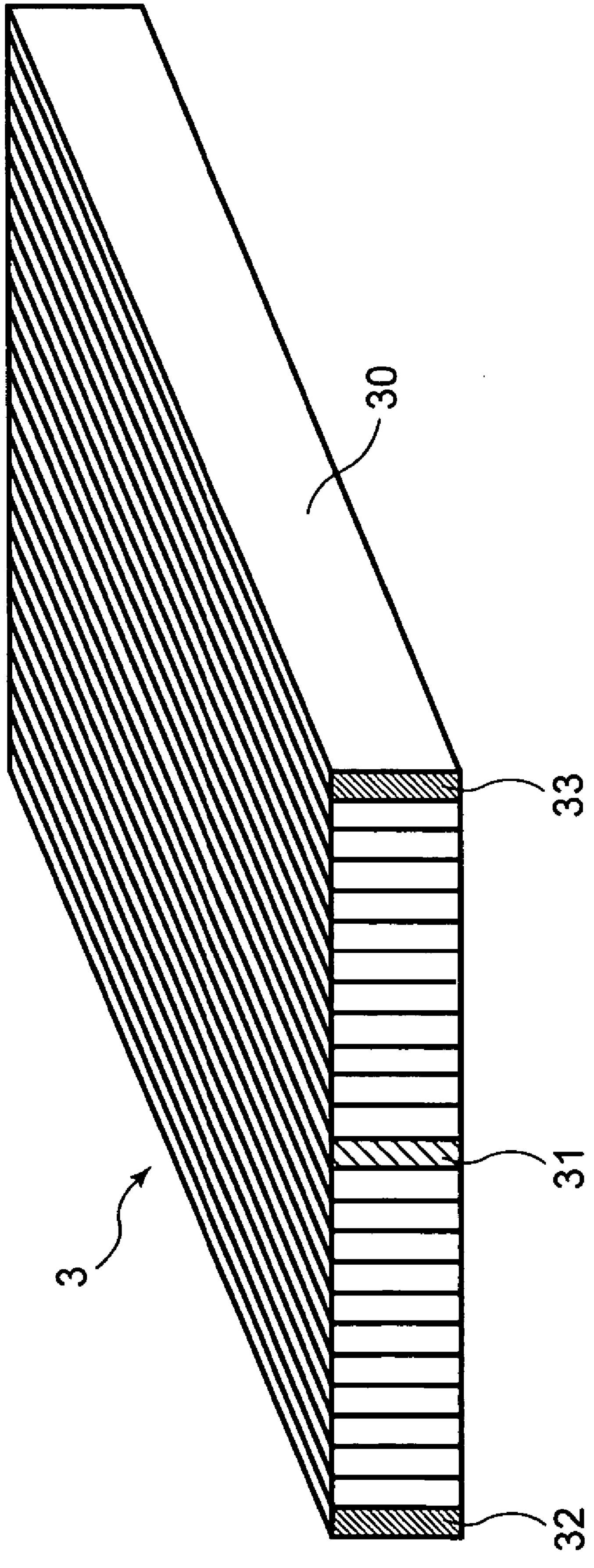
FIG. 2 is an illustration showing an exemplary configuration of a piezoelectric transducer according to the first embodiment.

The piezoelectric transducer 3 will be described in detail below. FIG. 2 is an illustration showing an exemplary configuration of the piezoelectric transducer 3 according to the first embodiment.

As shown in FIG. 2, the piezoelectric transducer 3 is formed of (or includes) a plurality of piezoelectric members 30 which are arrayed along the slice direction. Each piezoelectric member 30 maybe made of, for example, a composition of ceramic materials such as lead zirconate titanate ($Pb(Zr, Ti)O_3$), lithium niobate ($LiNbO_3$), barium titanate ($BaTiO_3$), and lead titanate ($PbTiO_3$) A composition of one piezoelectric member 30 may be identical to a composition of another one piezoelectric member 30 so that the one and another piezoelectric members 30 have substantially the same electromechanical coupling factor. Also, the composition of the one piezoelectric member 30 may be different from a composition of another piezoelectric member 30 so that those piezoelectric members 30 have different electromechanical coupling factors from each other. When the composition (first composition) of the one piezoelectric member 30 is different from the composition (second composition) of another piezoelectric member 30, the first composition may be made from the same ceramic materials as the second composition but in a different composition proportion from the second composition. Alternatively, when the first composition is different from the second composition, the first composition may be made from different ceramic materials from the second composition The electromechanical coupling factor is a coefficient showing transducing capability between electric energy and kinetic energy. The electromechanical coupling factor may be expressed in a square root of a ratio between generated kinetic energy and supplied electric energy or between generated electric energy and supplied kinetic energy.

A concrete electromechanical coupling factor which each piezoelectric member 30 has may be predetermined, for example, in accordance with a curve of a predetermined mathematical function such as, for example, a sine curve and a Gaussian curve. According to the curve, electromechanical coupling factors of the piezoelectric members 30 are weighted, respectively. That is, each of the piezoelectric members 30 is given a predetermined electromechanical coupling factor resulting from a composition of the each piezoelectric member 30. Therefore, the composition of each piezoelectric member 30 may be determined based on the determined (or weighted) electromechanical coupling factor.

Figure 3:
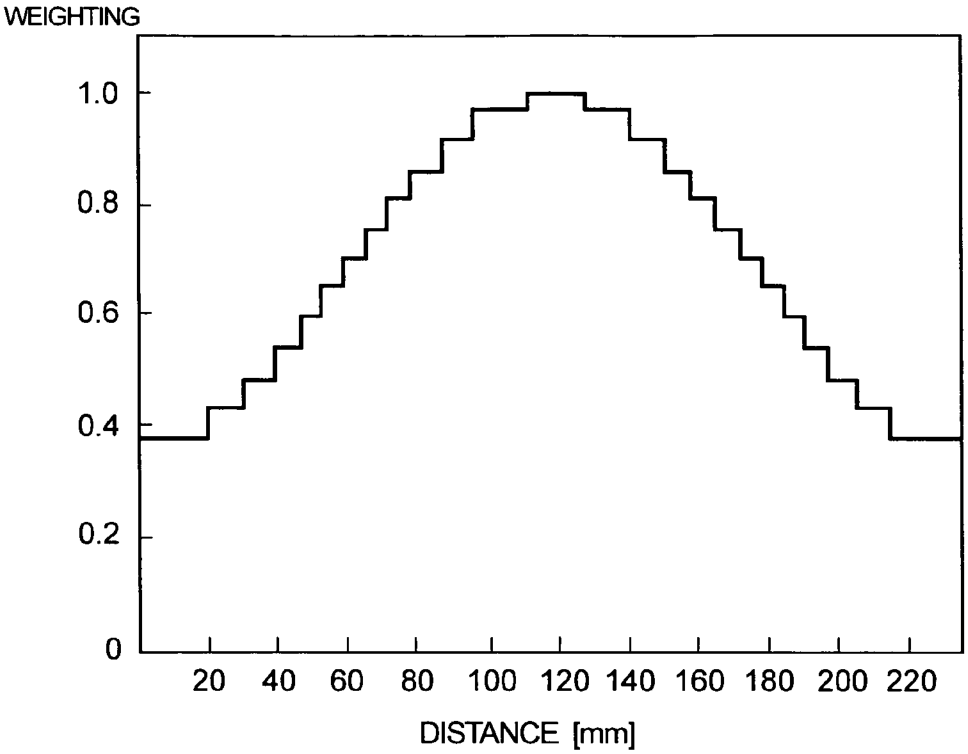
FIG. 3 is a chart showing an example of weighting according to the first embodiment.

FIG. 3 is a chart showing an example of the weighting according to the first embodiment. A horizontal axis in FIG. 3 represents arrayed positions of the piezoelectric members 30 along the slice direction. In other words, the horizontal axis represents the distance from one end of the piezoelectric transducer 3 (or one array end of the piezoelectric members 30) to the other end along the slice direction. A vertical axis in FIG. 3 represents the weighting effect. In the first embodiment, the maximum weighting is, for example, one (1.0) and is given to a piezoelectric member 31, shown in FIG. 2, of the piezoelectric members 30. The piezoelectric member 31 is positioned in the middle of the array of the piezoelectric members 30. The minimum weighting is, for example, approximately zero point four (0.4) and is given to piezoelectric members 32 and 33, shown in FIG. 2, of the piezoelectric members 30. The piezoelectric member 32 is positioned at one end of the array of the piezoelectric members 30. The piezoelectric member 33 is positioned at another end of the array. The weightings for the piezoelectric members 30 between the piezoelectric members 31 and 32 may preferably be substantially identical to the weightings for the piezoelectric members 30 between the piezoelectric members 31 and 33.

The weighting curve in FIG. 3 follows a curve of a specific mathematical function. Each step of the curve represents a weighting value for one piezoelectric member 30. A width of each step may be determined in accordance with the curve. This means that a width of each piezoelectric member 30 along the slice direction may be determined based on the width of the corresponding step. As a result of following the curve, one step may happen to correspond to two or more piezoelectric members 30. In other words, one piezoelectric member 30 may have substantially the same electromechanical coupling factor as the next piezoelectric member 30 in the array.

The electromechanical coupling factor of each piezoelectric member 30 is determined based on the weighting. In the above case, the electromechanical coupling factors of the piezoelectric members 32 and 33 are 0.4 times as high as the electromechanical coupling factor of the piezoelectric member 31. In the first embodiment, the piezoelectric member 31 has the highest electromechanical coupling factor. Both or either of the piezoelectric members 32 and 33 has the lowest electromechanical coupling factor. The piezoelectric members 30 positioned between the piezoelectric members 31 and 32 gradually decrease their electromechanical coupling factors towards the piezoelectric member 32 as understood from the curve shown in FIG. 3. Similarly, the piezoelectric members 30 positioned between the piezoelectric members 31 and 33 gradually decrease their electromechanical coupling factors towards the piezoelectric member 33 as understood from the curve shown in FIG. 3. Here, when the electromechanical coupling factors are gradually decreased, an electromechanical coupling factor of one piezoelectric member 30 may be substantially identical to an electromechanical coupling factor of the next piezoelectric member 30 on the decrease.

As described above, the electromechanical coupling factor can be changed by controlling proportions in the ceramic material composition. For example, when lead zirconate titanate ($Pb(Zr, Ti)O_3$) is included in the composition of the piezoelectric member 30, the electromechanical coupling factor can be changed by controlling the concentration of zircon (Zr) in the $Pb(Zr, Ti)O_3$.

Figure 4:
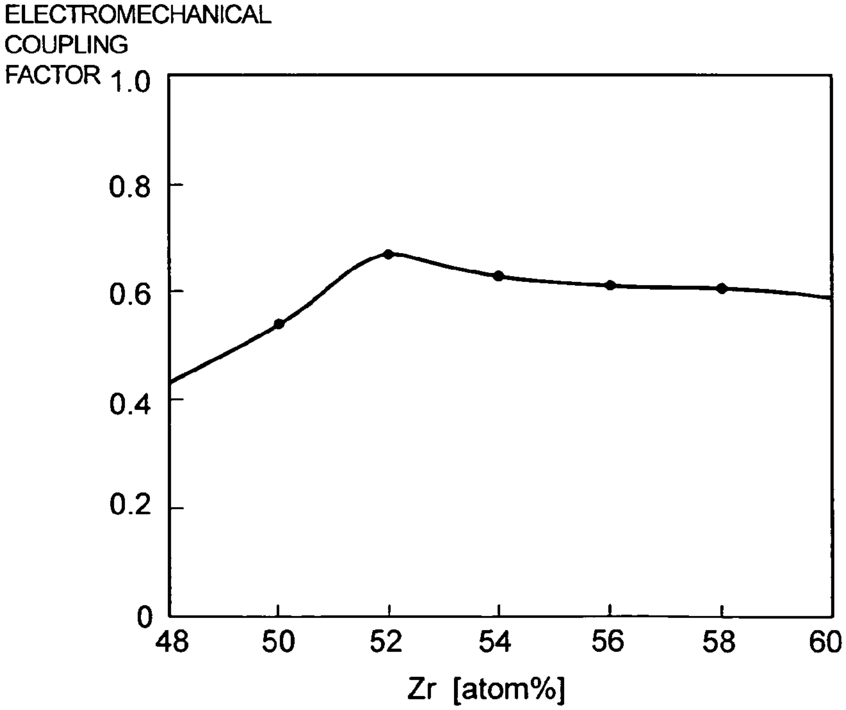
FIG. 4 is a chart showing a typical relationship between concentrations of zircon and electromechanical coupling factors.

FIG. 4 is a chart showing a typical relationship between concentrations of Zr and electromechanical coupling factors. As shown in FIG. 4, when the concentration is approximately 52 [atom %], the electromechanical coupling factor is approximately 0.7. Also when the concentration is 48 [atom %], the electromechanical coupling factor is approximately 0.4. As described above, since it is possible to change the electromechanical coupling factor by changing a composition of a ceramic material (e.g., $Pb(Zr, Ti)O_3$) (or changing the concentrations of Zr and/or titanium (Ti)), different weightings can be given to the piezoelectric members 30 by applying the ceramic material ($Pb(Zr, Ti)O_3$) in various compositions of Zr and Ti to the piezoelectric members 30.

Although the same ceramic material ($Pb(Zr, Ti)O_3$ in this embodiment) in different compositions has been described for the weightings, different ceramic materials may be used for the piezoelectric members 30, respectively. For example, $Pb(Zr, Ti)O_3$ may be used for the piezoelectric member 31 while $LiNbO_3$ may be used for the piezoelectric members 32 and 33, so as to accomplish preferable weightings.

Further in the first embodiment, frequency constants of the piezoelectric members 30 may be ranged within, for example, plus or minus ten percent (±10%) among the piezoelectric members 30. When a fundamental frequency constant is, for example, two thousand meters Hertz (2000 [m·Hz]), the piezoelectric members 30 may be prepared so that their frequency constants are ranged between one thousand and eight hundred meters Hertz (1800 [m·Hz]) and two thousand and two hundred meters Hertz (2200 [m·Hz]). Such a frequency constant range use may make it possible to obtain ultrasound pulses with almost the same frequency from each piezoelectric member 30.

Figure 5A:
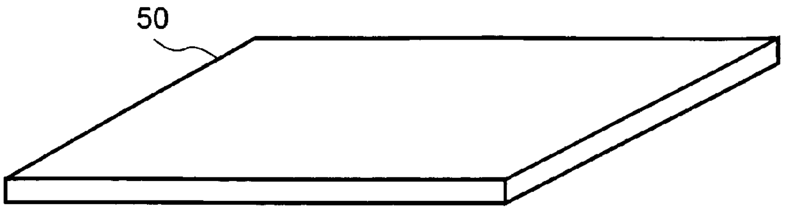
FIGS. 5A to 5C are illustrations showing exemplary manufacturing processes of the piezoelectric transducer according to the first embodiment.
Figure 5B:
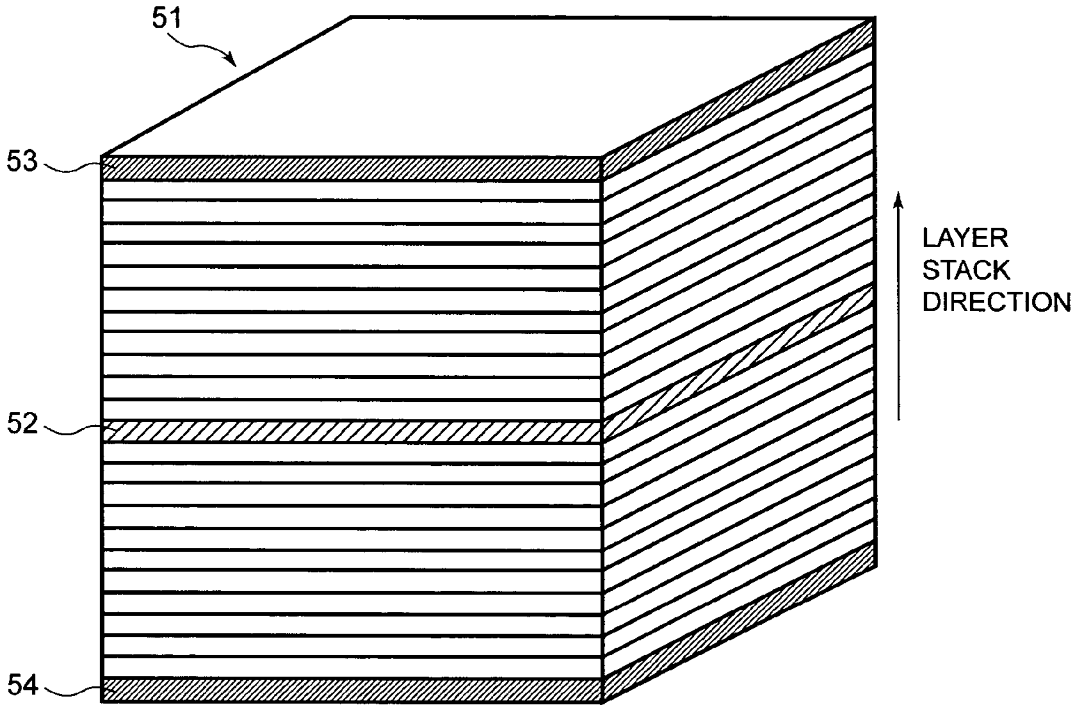
Figure 5C:
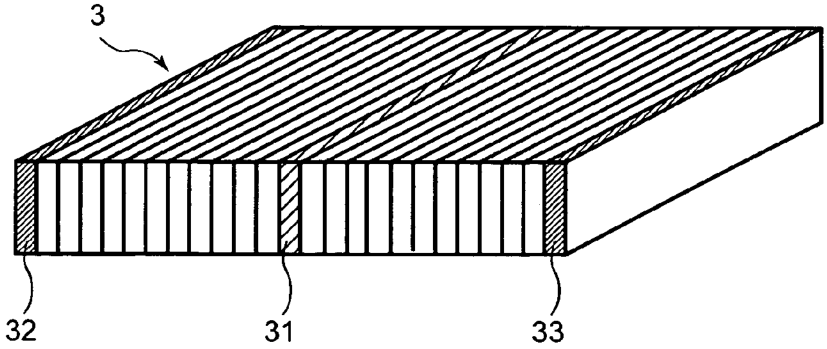

A manufacturing (or preparation) technique of the piezoelectric transducer 3 will be described with reference to FIGS. 5A to 5C. FIGS. 5A to 5C are illustrations showing exemplary manufacturing processes of the piezoelectric transducer 3 according to the first embodiment.

As shown in FIG. 5A, a green sheet 50 is provided. A part of one green sheet 50 corresponds to one piezoelectric member 30. First, one or more predetermined ceramic materials are pulverized so as to obtain a predetermined electromechanical coupling factor. The ceramic materials and their amount to be used are determined in a manner described in FIGS. 2 and 3. The pulverized ceramic materials are mixed with resin so as to prepare the green sheet 50 having the predetermined electromechanical coupling factor. The thickness of the green sheet 50 is determined in accordance with the width of a corresponding step in the curve of the mathematical function for the weighting, as shown in FIG. 3.

A plurality of such green sheets 50 are prepared and layered to make a ceramic block 51 as shown in FIG. 5B. In an example shown in FIG. 5B, the layered ceramic block 51 is formed of (or includes) 25 green sheets 50. There is a green sheet 52 in the middle of the layered ceramic block 51 along a layer stack direction. This layer stack direction is the same as the slice direction in FIG. 1. There are also green sheets 53 and 54 at one and the other ends of the layered ceramic block 51 along the layer stack direction. Further, the weightings of the electromechanical coupling factors may be symmetric between the green sheets 52 to 53 and the green sheets 52 to 54. When there is no identical electromechanical coupling factor between two green sheets 50 including 52, 53, and 54, which are positioned next to each other, 13 kinds of green sheets 50 are required for the layered ceramic block 51. Each of the 13 green sheets 50 has a different composition so as to have a required electromechanical coupling factor.

When the 25 green sheets 50 including 52, 53, and 54 have been prepared, these green sheets 50 are layered in accordance with their electromechanical coupling factors, and the layered ceramic block 51 is prepared. The electromechanical coupling factors gradually decrease towards the green sheets 53 and 54 from the green sheet 52. The layered ceramic block 51 is then sintered. As a result, a layered piezoelectric block is obtained.

As a modified technique of preparing the layered ceramic block, two or more of such 25 green sheet-blocks may be stacked along the layer stack direction. In more detail, two or more layered ceramic blocks 51 are prepared first. On top of the green sheet 53 of one layered ceramic block 51, another layered ceramic block 51 is placed. A resin sheet may be inserted into between the green sheet 53 of the one layered ceramic block 51 and the green sheet 54 of another layered ceramic block 51. Further more layered ceramic blocks 51 may be stacked along the layer stack direction. The stacked block is sintered as a whole. The thickness of the resin sheet may be determined to be appropriate for the width required to cut the stacked block along the resin sheet so as to obtain two or more independent layered piezoelectric blocks, each of which corresponding to the layered ceramic block 51.

When the layered piezoelectric block is obtained in the above manner, the layered piezoelectric block is cut into pieces along the layer stack direction (or along a direction perpendicular to the layer of the green sheets 51). Each piece can be used as the piezoelectric transducer 3 as shown in FIG. 5C. The piezoelectric member 31 is made of a part of the green sheet 52. Therefore, the piezoelectric member 31 has the highest electromechanical coupling factor in the piezoelectric transducer 3. The piezoelectric members 32 and 33 are made of the green sheets 53 and 54, respectively. Therefore, the piezoelectric members 32 and 33 have the lowest electromechanical coupling factor in the piezoelectric transducer 3.

Further, the piezoelectric transducer 3 may be polished along its thickness direction so that ultrasound pulses of a desired frequency are generated from the piezoelectric transducer 3. In other words, the piezoelectric transducer 3 may be polished so that the frequency constant can fall within, for example, a tolerance value of a plus or minus ten percent of the fundamental frequency constant although the frequency constant also depends on the selection or composition of the ceramic material. After the polish, electrodes 6 and 7 (not shown in FIG. 5C) are provided over one and the opposite surfaces of the piezoelectric transducer 3 to be faced with the back surface material 2 and the second acoustic matching layer 4*b* by a sputtering technique with gold (Au). The electrodes 6 and 7 are polarized. Accordingly, the piezoelectric transducer 3 may be prepared without a lot of manufacture processes. This can restrain a manufacture cost increase.

Although the 25 green sheets have been used to obtain the piezoelectric transducer 3 in the example shown in FIGS. 5A to 5C, the number of the green sheets is not limited to the above example. The more the green sheets are used, the more the weightings can be detailed. The curve, shown in FIG. 3, formed by the steps corresponding to the piezoelectric members 30 becomes smooth if more green sheets 51 are prepared. For example, 100 green sheets each of which having a thickness of approximately one hundred micrometers (100 [μm]) may be layered and sintered. In this case, it is possible to obtain a piezoelectric transducer having a ten-millimeter (10 [mm]) width along the slice direction.

Any mathematical function can be applied to the weightings as long as the highest weighting is given to the middle of the piezoelectric transducer 3 and the weightings gradually decrease towards both ends of the piezoelectric transducer 3 along the slice direction.

When electric signals are applied to the piezoelectric transducer 3 in the ultrasound transmission direction, acoustic pressure of ultrasound pulses to be transmitted is weighted in proportion to the electromechanical coupling factors given to the piezoelectric members 30. Similarly, acoustic pressure of received ultrasound pulses (echo signals) is also weighted in proportion to the electromechanical coupling factors given to the piezoelectric members 30. FIGS. 6A and 6B are charts showing distributions of acoustic pressure in the reception of a prior art ultrasonic transducer in which no weighting is applied. FIG. 7 is a chart showing distributions of acoustic pressure in the reception of the ultrasonic transducer 1 according to the first embodiment.

FIG. 6A shows the distributions at depths of ten millimeters (10 [mm]), twenty millimeters (20 [mm]), and thirty millimeters (30 [mm]) from an acoustic lens in the ultrasound transmission direction. FIG. 6B shows the distributions at depths of forty millimeters (40 [mm]) to one hundred millimeters (100 [mm]) by every ten millimeters (10 [mm]) from the acoustic lens in the ultrasound transmission direction. In FIGS. 6A and 6B, a horizontal axis represents the distance from the middle of a piezoelectric transducer along the slice direction. A vertical axis represents the acoustic pressure in the reception of a prior art ultrasonic transducer. FIG. 7 shows the distributions at depths of ten millimeters (10 [mm]) to one hundred millimeters (100 [mm]) by every ten millimeters (10 [mm]) from the acoustic lens 5 in the ultrasound transmission direction. In FIG. 7, a horizontal axis represents the distance from the middle of the arrayed piezoelectric members 30. A vertical axis represents the acoustic pressure in the reception of the ultrasonic transducer 1.

As shown in FIG. 6A, an ultrasound beam at each of the depth is not concentrated but spread around the middle of the piezoelectric transducer (i.e., around the distance of zero millimeter), compared to ultrasound beams in FIG. 6B. On the other hand, as shown in FIG. 6B, an ultrasound beam at each of the depth has higher side lobes, compared to the ultrasound beams in FIG. 6A. On the other hand, as shown in FIG. 7, an ultrasound beam at each of the depth is concentrated with a narrowed down main lobe at the middle of the arrayed piezoelectric members 30 (or the middle of the piezoelectric transducer 3). At the same time, the side lobes of the ultrasound beam at each of the depth are kept low.

Therefore, compared to the prior art ultrasonic transducer without the weighting, it may be possible to improve sensitivity of the ultrasonic transducer 1. Since the weightings are accomplished by characteristics of the piezoelectric members 30 per se, the ultrasonic transducer 1 may not require any additional components or physical or electrical processing. This results in preventing the size of the ultrasonic transducer 1 from becoming large while the weightings are accomplished. Also, the thickness of scan slices (i.e., the thickness of a scan plane along the slice direction) may be more uniformed along the ultrasound transmission direction (along a depth direction of the patient' body). Therefore, ultrasound images obtained based on the ultrasonic scan can be improved in their image quality. Furthermore, the ultrasonic transducer 1 can be applied to any type of ultrasonic probes.

Second Embodiment

In the first embodiment, the piezoelectric members 30 are made of compositions giving predetermined electromechanical coupling factors so as to provide appropriate weightings corresponding to a specific function. Piezoelectric members in the second embodiment are, however, made of compositions giving predetermined relative dielectric constants so as to provide appropriate weightings. A configuration of the ultrasonic transducer according to the second embodiment may be similar to that shown in FIGS. 1 and 2. Therefore, the ultrasonic transducer according to the second embodiment will be described with reference to FIGS. 1 and 2. The explanation of FIGS. 1 and 2 which can also be applied to the second embodiment will be omitted herein.

FIG. 8 is a chart showing an example of the weighting according to the second embodiment. As shown in FIG. 8, the stepped curve is in a form opposite to the curve shown in FIG. 3. That is, the curve in FIG. 8 follows a curve of a mathematical function which can be an inverse function of the function applied in the first embodiment. A horizontal axis in FIG. 8 represents arrayed positions of the piezoelectric members 30 along the slice direction. In other words, the horizontal axis represents the distance from one end of the piezoelectric transducer 3 (or one array end of the piezoelectric members 30) to the other end along the slice direction. A vertical axis in FIG. 8 represents the weighting. In the second embodiment, the maximum weighting is, for example, one (1.0) and is given to the piezoelectric members 32 and 33. The minimum weighting is, for example, approximately zero point four (0.4) and is given to the piezoelectric member 31. The weightings for the piezoelectric members 30 between the piezoelectric members 31 and 32 may preferably be substantially identical to the weightings for the piezoelectric members 30 between the piezoelectric members 31 and 33.

The weighting curve in FIG. 8 follows a curve of a specific mathematical function. Similar to FIG. 3, each step of the curve represents a weighting for one piezoelectric member 30. A width of each step may be determined in accordance with the curve. This means that a width of each piezoelectric member 30 along the slice direction may be determined based on the width of the corresponding step. As a result of following the curve, one step may happen to correspond to two or more piezoelectric members 30. In other words, one piezoelectric member 30 may have substantially the same relative dielectric constant as the next piezoelectric member 30 in the array.

The relative dielectric constant of each piezoelectric member 30 is determined based on the weighting. In the above case, the relative dielectric constant of the piezoelectric member 31 is 0.4 times as high as the relative dielectric constants of the piezoelectric members 32 and 33. In the second embodiment, the piezoelectric member 31 has the lowest relative dielectric constant. Both or either of the piezoelectric members 32 and 33 has the highest relative dielectric constant. The piezoelectric members 30 positioned between the piezoelectric members 31 and 32 gradually increase their relative dielectric constants towards the piezoelectric member 32 as understood from the curve shown in FIG. 8. Similarly, the piezoelectric members 30 positioned between the piezoelectric members 31 and 33 gradually increase their relative dielectric constants towards the piezoelectric member 33 as understood from the curve shown in FIG. 8. Here, when the electromechanical coupling factors are gradually increased, a relative dielectric constant of one piezoelectric member 30 may be substantially identical to a relative dielectric constant of the next piezoelectric member 30 on the increase.

As similar to the first embodiment, the relative dielectric constant can be changed by controlling proportions in the ceramic material composition. For example, when the lead zirconate titanate ($Pb(Zr, Ti)O_3$) is included in the composition of the piezoelectric member 30, the relative dielectric constant can be changed by controlling the concentration of zircon (Zr) in the $Pb(Zr, Ti)O_3$.

FIG. 9 is a chart showing a typical relationship between concentrations of Zr and relative dielectric constants. As shown in FIG. 9, since it is possible to change the relative dielectric constant by changing a composition of a ceramic material (e.g., $Pb(Zr, Ti)O_3$) (or changing the concentrations of Zr and/or titanium (Ti)), different weightings can be given to the piezoelectric members 30 by applying the ceramic material ($Pb(Zr, Ti)O_3$) in various compositions of Zr and Ti to the piezoelectric members 30. As similar to the first embodiment, different ceramic materials may be used for the piezoelectric members 30, respectively.

Also in the second embodiment, frequency constants of the piezoelectric members 30 may be ranged within, for example, a tolerance value of plus or minus ten percent (±10%) among the piezoelectric members 30. Such a frequency constant range use may make it possible to obtain ultrasound pulses with almost the same frequency from each piezoelectric member 30.

When electric signals are applied to the piezoelectric transducer 3 in the ultrasound transmission direction, acoustic pressure of ultrasound pulses to be transmitted is weighted in proportion to the relative dielectric constants given to the piezoelectric members 30. In contrast, acoustic pressure of received ultrasound pulses (echo signals) is weighted in inverse proportion to the relative dielectric constants given to the piezoelectric members 30. In the ultrasound transmission, there may be obtained distributions of acoustic pressure in which acoustic pressure is low around the middle of the piezoelectric transducer 3 (i.e., around the distance of zero millimeter) and is high at both ends of the piezoelectric transducer 3. That is, the obtained distributions may have higher side lobes and a narrowed-down main lobe. In the ultrasound reception, there may be obtained distributions of acoustic pressure in which side lobes are kept low and a main lobe is well narrowed down.

Figure 10A:
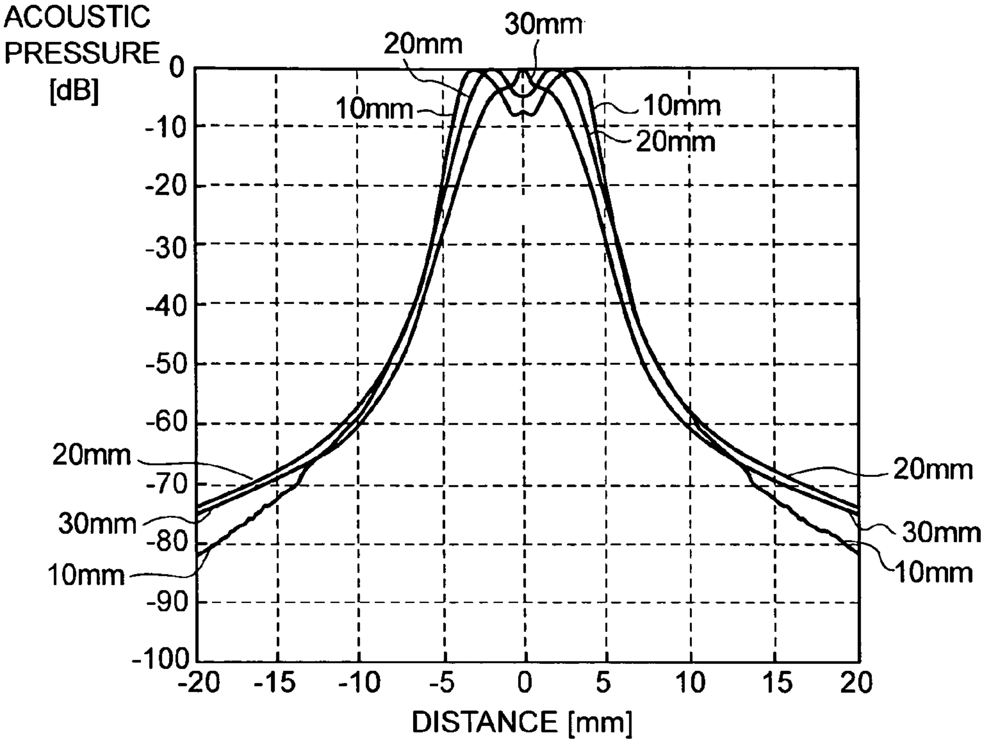
FIGS. 10A and 10B are charts showing distributions of acoustic pressure in the reception of the ultrasonic transducer according to the second embodiment.
Figure 10B:
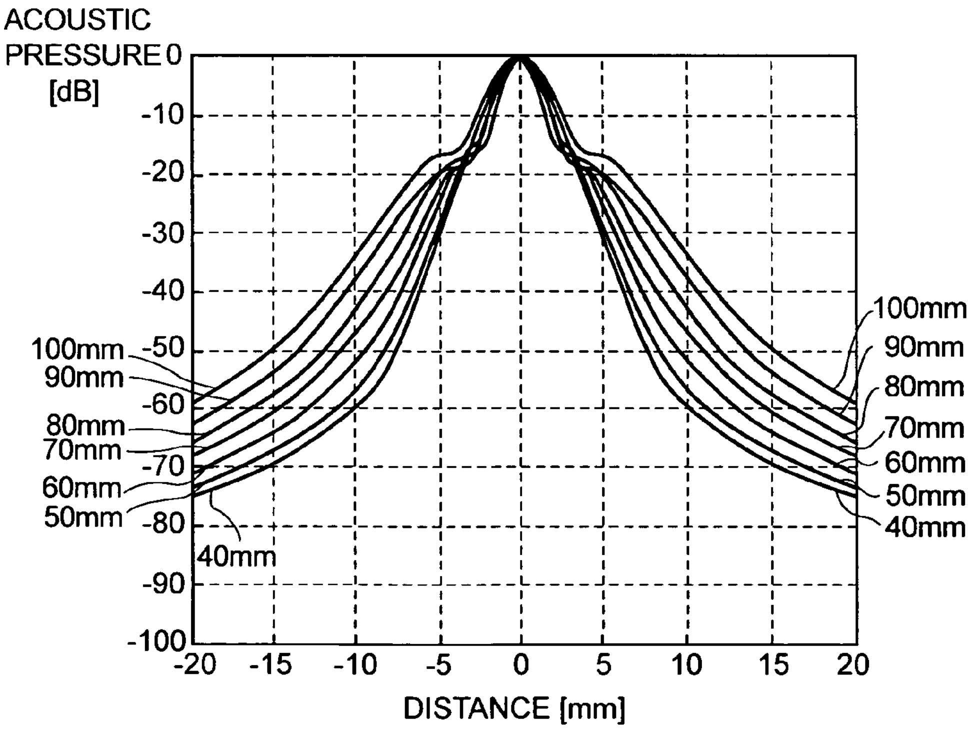

FIGS. 10A and 10B are charts showing the distributions of acoustic pressure in the reception of the ultrasonic transducer 1 according to the second embodiment. FIG. 10A shows the distributions at depths of ten millimeters (10 [mm]), twenty millimeters (20 [mm]), and thirty millimeters (30 [mm]) from the acoustic lens 5 in the ultrasound transmission direction. FIG. 10B shows the distributions at depths of forty millimeters (40 [mm]) to one hundred millimeters (100 [mm]) by every ten millimeters (10 [mm])

from the acoustic lens 5 in the ultrasound transmission direction. A horizontal axis represents the distance from the middle of the arrayed piezoelectric members 30. A vertical axis represents the acoustic pressure in the reception of the ultrasonic transducer 1. Compared to the prior art ultrasonic transducer without the weighting, the main lobe is well narrowed down in FIG. 10B.

Usually, when ultrasound pulses are transmitted at a fundamental frequency, harmonic components which frequencies are integer multiple of the fundamental frequency may be caused as the ultrasound pulses run through the patient's body. When an ultrasound diagnosis apparatus with a THI (Tissue Harmonic Imaging) feature is used with an ultrasonic probe including the ultrasonic transducer 1 according to the second embodiment, the ultrasonic transducer 1 transmits ultrasound pulses at the fundamental frequency and may receive echo signals including harmonic components caused in the patient's body. In such a case, the distributions of acoustic pressure in the reception of the ultrasonic transducer 1 show low side lobes and a well narrowed-down main lobe. The THI feature is known as a technique of extracting only the harmonic components and imaging the extracted harmonic components. Since the harmonic components appear more frequently at the high acoustic pressure, it is advantageous that the ultrasonic transducer 1 enhances the main lobe and reduces the side lobes. As a result, the distributions at depths of ten millimeters (10 [mm]), twenty millimeters (20 [mm]), and thirty millimeters (30 [mm]) shown in FIG. 10A have reduced side lobes and narrowed-down main lobes.

Figure 11:
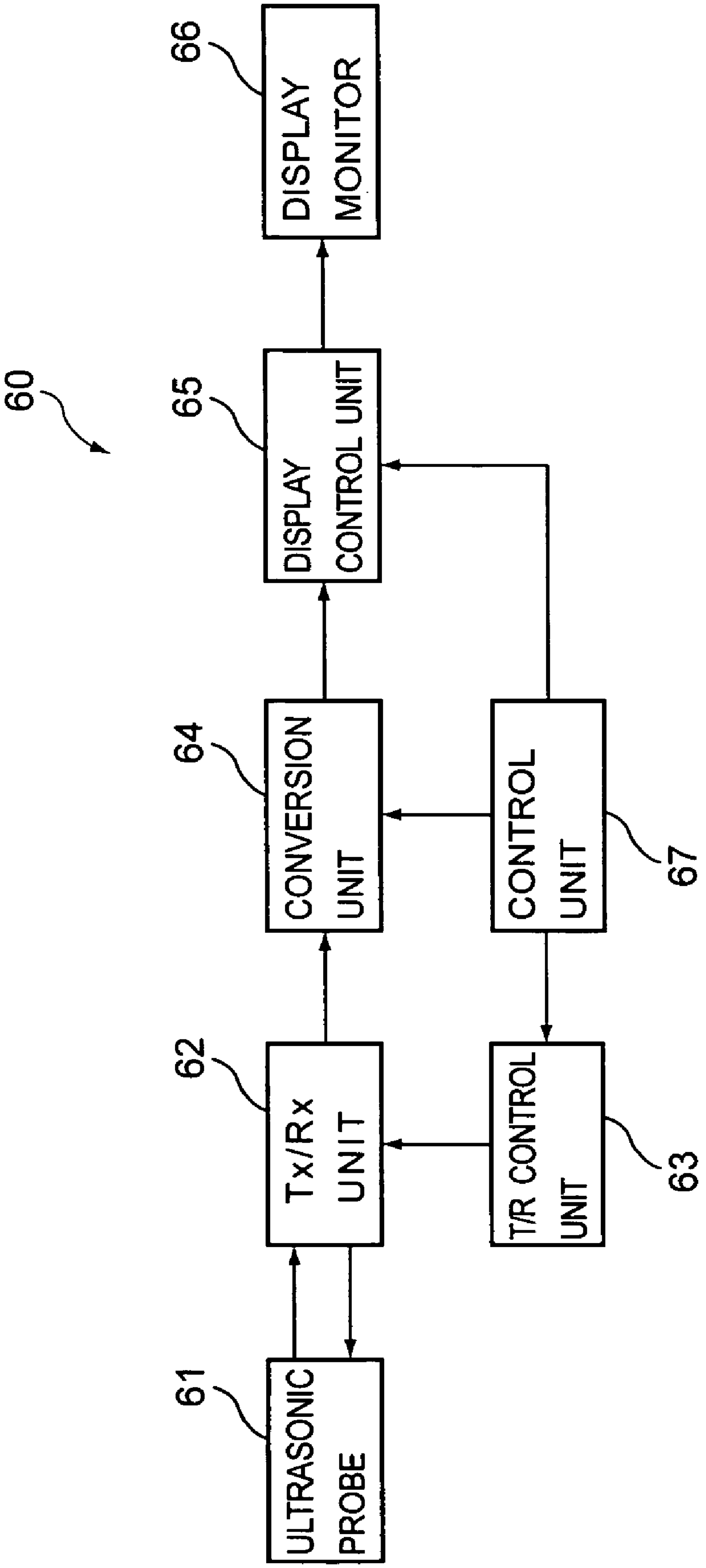
FIG. 11 is a block diagram showing an exemplary configuration of an ultrasound imaging apparatus having the ultrasonic transducer of FIG. 1.

FIG. 11 is a block diagram showing an exemplary configuration of an ultrasound imaging apparatus having the ultrasonic transducer of FIG. 1. An ultrasound diagnosis apparatus will be explained as an example of the ultrasound imaging apparatus.

As shown in FIG. 11, an ultrasound diagnosis apparatus 60 includes an ultrasound probe 61, a transmission and reception unit 62, a transmission and reception control unit 63, a conversion unit 64, a display control unit 65, a display monitor 66, and a control unit 67. The ultrasonic transducer 1 described in the above first or second embodiment is incorporated in the ultrasonic probe 61. The above elements other than the ultrasonic probe 61 may be provided in a main unit of the ultrasound diagnosis apparatus 60. The ultrasonic probe 61 may be connected to the main unit through its cable. The ultrasonic transducer 1 is activated to generate ultrasound pulses by the transmission and reception unit 62.

The transmission and reception unit 62 provides the ultrasonic probe 61 with electric signals so that the ultrasonic transducer 1 generates the ultrasound pulses. The transmission and reception unit 62 also receives the echo signals received by the ultrasonic transducer 1. As described in the first embodiment, the electric signals are applied to the ultrasonic transducer 1 incorporated in the ultrasonic probe 61.

The ultrasound pulses are generated from the ultrasonic transducer 1 and a retransmitted to the inside of the patient's body. The transmitted ultrasound pulses result in echo signals. The echo signals resulting from the ultrasound pulses return from the inside of the patient's body and are received by the ultrasonic transducer 1 incorporated in the ultrasonic probe 61. The echo signals are caused by acoustic impedance mismatching inside the patient's body.

The transmission and reception control unit 63 controls the transmission and the reception of the transmission and reception unit 62. The conversion unit 64 processes the echo signals received by the transmission and reception unit 62 so as to convert the echo signals into ultrasound image data of the patient. The display control unit 65 controls the display monitor 66 to display ultrasound images based on the ultrasound image data. The display monitor 66 displays the ultrasound images. The control unit 67 controls over the ultrasound diagnosis apparatus 60. For example, the control unit 67 may be connected to the transmission and reception control unit 63, the conversion unit 64, and the display control unit 65, and control these units.

According to the ultrasound diagnosis apparatus, it may be possible to obtain improved ultrasound images, compared to the prior art apparatus, since the side lobes are kept low and the main lobe is narrowed down in the acoustic pressure distribution, which results in an almost even acoustic field whether at near or far (or deep or shallow) positions from the ultrasonic transducer 1.

The embodiments described above are examples described only for making it easier to understand the present invention, and are not described for the limitation of the present invention. Consequently, each component and element disclosed in the embodiments of the present invention may be redesigned or modified to its equivalent within a scope of the present invention Furthermore, any possible combination of such components and elements may be included in a scope of the present invention as long as an advantage similar to those obtained according to the above disclosure in the embodiments of the present invention is obtained.

Numerous modifications and variations of the present invention are possible in light of the above teachings. It is therefore to be understood that within the scope of the appended claims, the invention may be practiced otherwise than as specifically described herein.

The invention claimed is:

1. A piezoelectric transducer for an ultrasonic scan, comprising:

a plurality of piezoelectric members arrayed in direct contact along a direction perpendicular to a scan plane by the ultrasonic scan, the plurality of piezoelectric members are made of predetermined compositions so as to have predetermined electromechanical coupling factors, and are arrayed in an order that the predetermined electromechanical coupling factors gradually decrease towards one and the other ends of the array from a middle of the array.

2. The transducer according to claim 1, wherein the predetermined electromechanical coupling factors have a symmetric set of values to the one end of the array and the other end of the array with respect to the middle of the array.

3. The transducer according to claim 1, wherein the predetermined electromechanical coupling factors are based on a curve of a predetermined mathematical function.

4. The transducer according to claim 3, wherein a width, along the slice direction, of each of the plurality of piezoelectric members is determined in accordance with the curve.

5. A piezoelectric transducer for an ultrasonic scan, comprising:

a plurality of piezoelectric members arrayed in direct contact along a direction perpendicular to a scan plane by the ultrasonic scan, wherein a first piezoelectric member positioned in a middle of the plurality of piezoelectric members is made of a first composition so as to have a first electromechanical coupling factor;

a second piezoelectric member positioned at one end of the plurality of piezoelectric members is made of a second composition so as to have a second electromechanical coupling factor, the second electromechanical coupling factor being lower than the first electromechanical coupling factor;

a third piezoelectric member positioned at the other end of the plurality of piezoelectric members is made of a third composition so as to have a third electromechanical coupling factor, the third electromechanical coupling factor being lower than the first electromechanical coupling factor;

a fourth piezoelectric member of the plurality of piezoelectric members, positioned between the first and second piezoelectric members, is made of a fourth composition so as to have a fourth electromechanical coupling factor, the fourth electromechanical coupling factor being lower than the first electromechanical coupling factor and higher than the second electromechanical coupling factor;

a fifth piezoelectric member of the plurality of piezoelectric members, positioned between the first and third piezoelectric members, is made of a fifth composition so as to have a fifth electromechanical coupling factor, the fifth electromechanical coupling factor being lower than the first electromechanical coupling factor and higher than the third electromechanical coupling factor;

a sixth piezoelectric member of the plurality of piezoelectric members, positioned between the first and fourth piezoelectric members, is made of a sixth composition so as to have a sixth electromechanical coupling factor, the sixth electromechanical coupling factor being lower than the first electromechanical coupling factor and substantially identical to or higher than the fourth electromechanical coupling factor; and a seventh piezoelectric member of the plurality of piezoelectric members, positioned between the first and fifth piezoelectric members, is made of a seventh composition so as to have a seventh electromechanical coupling factor, the seventh electromechanical coupling factor being lower than the first electromechanical coupling factor and substantially identical to or higher than the fifth electromechanical coupling factor.

6. The transducer according to claim 5, wherein the sixth composition is substantially identical to the fourth composition when the sixth electromechanical coupling factor is substantially identical to the fourth electromechanical coupling factor.

7. The transducer according to claim 5, wherein the seventh composition is substantially identical to the fifth composition when the seventh electromechanical coupling factor is substantially identical to the fifth electromechanical coupling factor.

8. The transducer according to claim 5, wherein the second electromechanical coupling factor is substantially identical to the third electromechanical coupling factor.

9. The transducer according to claim 5, wherein electromechanical coupling factors of the plurality of piezoelectric members are based on a curve of a predetermined mathematical function.

10. The transducer according to claim 9, wherein a width, along the slice direction, of each of the plurality of piezoelectric members is determined in accordance with the curve.

11. An ultrasonic transducer for an ultrasonic scan, comprising:

a piezoelectric transducer configured to generate an ultrasound, the piezoelectric transducer including a plurality of piezoelectric members arrayed in direct contact along a direction perpendicular to a scan plane by the ultrasonic scan;

a pair of electrodes configured to activate the piezoelectric transducer when a predetermined voltage is applied to the electrodes, the electrodes being provided on one and the opposite sides of the piezoelectric transducer, perpendicular to the array and the scan plane; and an acoustic lens provided on one side of one of the electrodes opposite to a side where the one electrode faces the piezoelectric transducer, wherein the generated ultrasound is transmitted through the acoustic lens, wherein the plurality of piezoelectric members are made of predetermined compositions so as to have predetermined electromechanical coupling factors, and are arrayed in an order that the predetermined electromechanical coupling factors gradually decrease towards one and the other ends of the array from a middle of the array.

12. An ultrasonic probe, connectable to a main unit of an ultrasound imaging apparatus, the probe comprising:

an ultrasonic transducer configured to perform an ultrasonic scan, the ultrasonic transducer including a piezo electric transducer, a first electrode facing to one side of the piezoelectric transducer, and a second electrode facing to the opposite side of the piezoelectric transducer, wherein the piezoelectric transducer includes a plurality of piezoelectric members arrayed in direct contact along a direction perpendicular to a scan plane by the ultrasonic scan, and the plurality of piezoelectric members are made of predetermined compositions so as to have predetermined electromechanical coupling factors and are arrayed in an order that the predetermined electromechanical coupling factors gradually decrease towards one and the other ends of the array from a middle of the array.

13. An ultrasound imaging apparatus, comprising:

an ultrasonic probe, including a piezoelectric transducer, configured to perform an ultrasonic scan; and a main unit coupled to the ultrasonic probe, the main unit having a processor configured to process a data obtained from the ultrasonic scan, wherein the piezoelectric transducer includes a plurality of piezoelectric members arrayed in direct contact along a direction perpendicular to a scan plane by the ultrasonic scan, and the plurality of piezoelectric members are made of predetermined compositions so as to have predetermined electromechanical coupling factors, and are arrayed in an order that the predetermined electromechanical coupling factors gradually decrease towards one and the other ends of the array from a middle of the array.

14. A method for making a plurality of piezoelectric transducers, the method comprising:

preparing a plurality of piezoelectric sheets made of predetermined compositions so as to have predetermined electromechanical coupling factors;

layering the plurality of piezoelectric sheets in an order that the predetermined electromechanical coupling factors gradually decrease towards one and the other ends of the layer from a middle of the layer;

sintering the layered piezoelectric sheets so as to obtain a layered piezoelectric block;

cutting the layered piezoelectric block, along a direction perpendicular to the layer, into the plurality of piezoelectric transducers, each of the piezoelectric transducers having an array of a plurality of piezoelectric members, arranged to be in direct contact along a direction perpendicular to a scan plane by an ultrasonic scan;

providing a first electrode on first surfaces of each of the plurality of piezoelectric transducers;

providing a second electrode on second surfaces of each of the plurality of piezoelectric transducers; and polarizing the transducers.

* * * * *

UNITED STATES PATENT AND TRADEMARK OFFICE

CERTIFICATE OF CORRECTION

PATENT NO. : 7,309,947 B2
APPLICATION NO. : 10/883733
DATED : December 18, 2007
INVENTOR(S) : Takashi Takeuchi et al.

It is certified that error appears in the above-identified patent and that said Letters Patent is hereby corrected as shown below:

On the title page, Item (75), the Inventors information is incorrect. Item (75) should read as follows:

-- Inventors: Takashi Takeuchi, Tochigi-ken (JP);
Tomohisa Imamura, Tochigi-ken, (JP);
Takashi Ogawa, Tochigi-ken, (JP) --

Signed and Sealed this

Twenty-ninth Day of April, 2008

JON W. DUDAS
*Director of the United States Patent and Trademark Office*